United States Patent
Arthur et al.

(10) Patent No.: US 9,439,702 B2
(45) Date of Patent: Sep. 13, 2016

(54) BONE FRACTURE REDUCTION SYSTEM AND METHODS OF USING THE SAME

(71) Applicant: KYPHON SARL, Neuchatel (CH)

(72) Inventors: Amy L. Arthur, Mountain View, CA (US); Mojan Goshayeshgar, Atherton, CA (US); Michael A. Smith, San Jose, CA (US)

(73) Assignee: KYPHON SÀrl, Neuchâtel (CH)

( * ) Notice: Subject to any disclaimer, the term of this patent is extended or adjusted under 35 U.S.C. 154(b) by 0 days.

(21) Appl. No.: 14/638,173

(22) Filed: Mar. 4, 2015

(65) Prior Publication Data

US 2015/0173817 A1  Jun. 25, 2015

Related U.S. Application Data

(63) Continuation of application No. 13/791,391, filed on Mar. 8, 2013, now Pat. No. 9,028,464.

(51) Int. Cl.
| | |
|---|---|
| A61B 17/88 | (2006.01) |
| A61B 17/86 | (2006.01) |
| A61B 17/16 | (2006.01) |
| A61B 17/34 | (2006.01) |

(52) U.S. Cl.
CPC ....... *A61B 17/8805* (2013.01); *A61B 17/1615* (2013.01); *A61B 17/1637* (2013.01); *A61B 17/3472* (2013.01); *A61B 17/864* (2013.01); *A61B 17/8855* (2013.01)

(58) Field of Classification Search
CPC .......................... A61B 17/864; A61B 17/8805
USPC .................. 606/86 R, 92–94, 105, 300–331
See application file for complete search history.

(56) References Cited

U.S. PATENT DOCUMENTS

| | | | |
|---|---|---|---|
| 6,679,886 B2 * | 1/2004 | Weikel | A61B 17/1671 606/167 |
| 7,623,902 B2 | 11/2009 | Pacheco | |
| 7,670,374 B2 | 3/2010 | Schaller | |
| 7,927,339 B2 | 4/2011 | Ralph et al. | |
| 8,167,884 B2 | 5/2012 | Pacheco | |
| 8,214,014 B2 | 7/2012 | Pacheco | |
| 8,313,492 B2 | 11/2012 | Wong et al. | |
| 8,366,717 B1 * | 2/2013 | Jordan | A61B 17/7098 606/94 |
| 8,372,126 B2 * | 2/2013 | Trieu | A61B 17/7098 606/304 |
| 2002/0099385 A1 | 7/2002 | Ralph et al. | |
| 2004/0225292 A1 * | 11/2004 | Sasso | A61B 17/8615 606/916 |

(Continued)

*Primary Examiner* — Christopher Beccia
(74) *Attorney, Agent, or Firm* — Sorell Lenna & Schmidt LLP

(57) ABSTRACT

A method of treating a fracture includes creating an access path to a fracture site in a bone and inserting a guidewire through the access path into the fracture site is provided. The method includes the steps of positioning a cannulated drill bit having a distal end including helical flutes configured for drilling through bone over the guidewire into the fracture site, and advancing the drill bit to create a passageway in the bone configured to receive a screw. Positioning a cannulated inflatable bone tamp over the guidewire and inflating the inflatable bone tamp to compress at least a portion of the bone in or near the fracture site so as to create a void. Delivering a bone void filler into the void through the access path to fill the void. Systems and kits are disclosed.

20 Claims, 6 Drawing Sheets

(56) References Cited

U.S. PATENT DOCUMENTS

| | | | | |
|---|---|---|---|---|
| 2005/0137604 A1* | 6/2005 | Assell | ................ | A61B 17/7074 606/93 |
| 2009/0264892 A1* | 10/2009 | Beyar | ................ | A61B 17/7095 606/94 |
| 2010/0030135 A1* | 2/2010 | Mitchell | ............... | A61M 31/00 604/48 |
| 2010/0125240 A1* | 5/2010 | Spedden | ............ | A61B 17/0057 604/37 |

* cited by examiner

BONE FRACTURE REDUCTION SYSTEM AND METHODS OF USING THE SAME

CROSS REFERENCE TO RELATED APPLICATIONS

This application is a continuation of U.S. patent application Ser. No. 13/791,391, filed on Mar. 8, 2013, which is incorporated herein by reference, in its entirety.

TECHNICAL FIELD

The present disclosure relates generally to instruments and devices for treating fractures. Methods of using such devices are also provided.

BACKGROUND

Fractures of the distal radius, such as, for example, Colles' fracture, comprise a substantial portion of all traumatic bone fractures. Surgical treatments may involve reduction with metal bone tamps or elevators, and fracture fixation with percutaneous pins, external fixation, or plate/screw implants. Surgical treatments often employ an open approach in all patients, including the elderly.

In a kyphoplasty procedure, an inflatable balloon tamp (IBT) is inserted inside a fractured vertebral body. The IBT is inflated to create a cavity that is filled with bone void filler, such as, for example, bone cement to restore height of the vertebral body. IBTs hold promise for an improved method of distal radius fracture treatment. An IBT may be used to percutaneously reduce simple Colles' fractures and create a well-defined void for delivery of bone void filler, which may be used in conjunction with percutaneous pins, ex-fix, plates or screws for fracture fixation.

SUMMARY

In one embodiment, in accordance with the principles of the present disclosure, a method of treating a fracture is provided. The method includes the steps of creating an access path to a fracture site in a bone and then inserting a guidewire through the access path into the fracture site. Positioning a cannulated drill bit having a distal end including helical flutes configured for drilling through bone over the guidewire into the fracture site, and advancing the drill bit to create a passageway in the bone configured to receive a screw. Positioning a cannulated inflatable bone tamp over the guidewire and inflating the inflatable bone tamp to compress at least a portion of the bone in the fracture site so as to create a void. Once the void is created, a bone void filler is delivered into the void through the access path to at least partially fill the void.

In one embodiment, in accordance with the principles of the present disclosure, a method for treating a distal radius fracture is provided. The method includes creating an access path to a fracture site in a bone and then inserting a guidewire through the access path and anchoring a distal end of the guidewire to the bone. A cannulated drill bit having a distal end including helical flutes configured for drilling through bone is positioned over the guidewire and through the cannula into the fracture site, and the drill bit is advanced to create a passageway in the bone configured to receive a cannulated screw. The cannulated drill bit is removed from the fracture site and then a cannulated inflatable bone tamp is positioned over the guidewire and the inflatable bone tamp is inflated to compress at least a portion of the bone in the fracture site so as to create at least one void. The inflatable bone tamp is then repositioned along the guidewire and inflated to create at least one additional void in the fracture site. The cannulated screw is positioned over the guidewire through the passageway created by the drill bit and the cannulated screw is anchored into the bone. The cannulated screw comprises fenestrations along its length. A bone void filler delivery tool then delivers bone void filler into the at least one void and the at least one additional void in the fracture site.

In one embodiment, in accordance with the principles of the present disclosure, a kit for treating a fracture is provided. The kit includes a guidewire, a cannulated drill bit having a distal end including helical flutes configured for drilling through bone to create a passageway, a cannulated inflatable bone tamp configured for positioning over the guidewire, a cannulated screw configured to fit within the passageway, and bone void filler.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
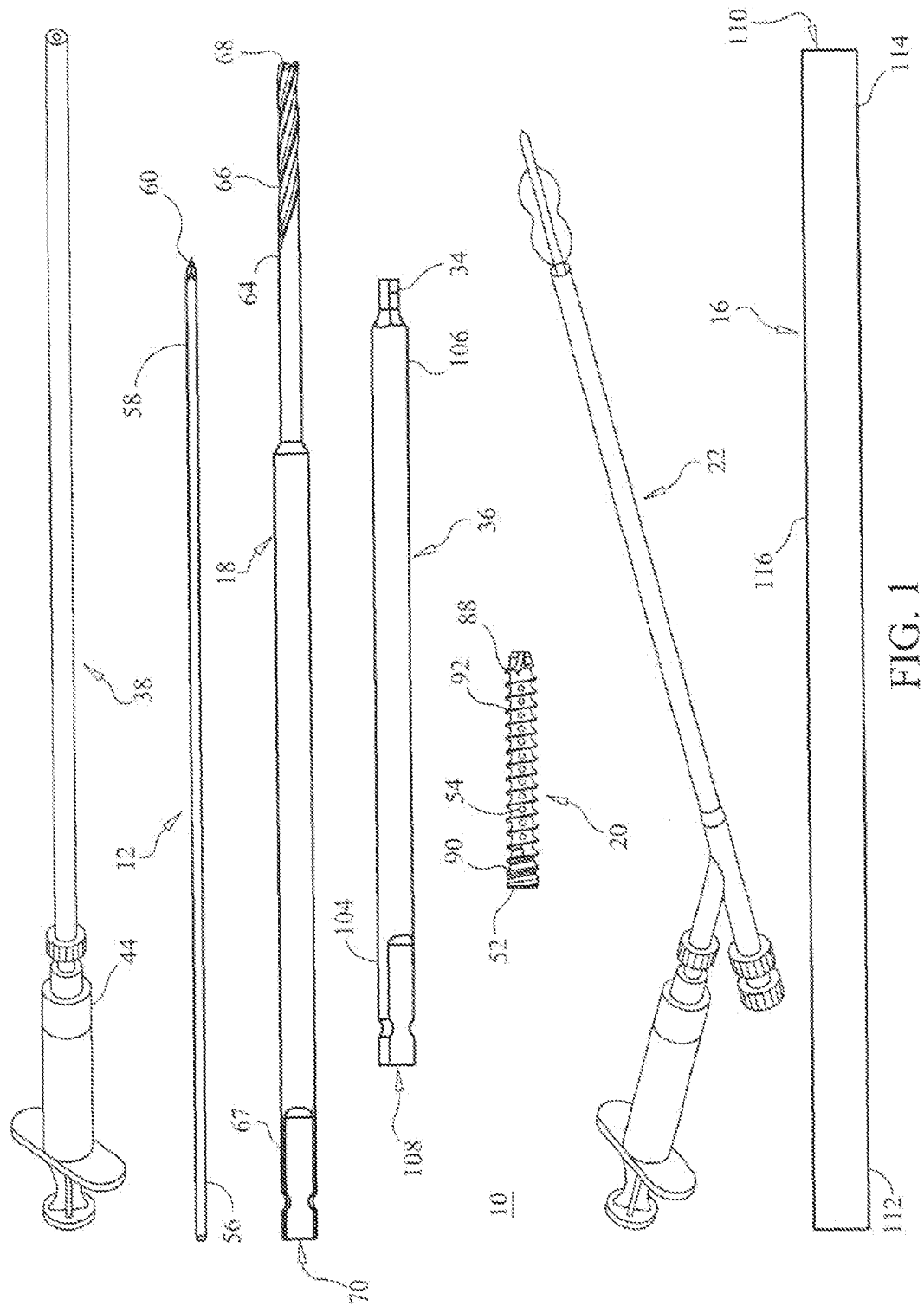
FIG. 1 is a perspective view of components of a system in accordance with the principles of the present disclosure.

The exemplary embodiments of the surgical system are discussed in terms of medical devices for the treatment of musculoskeletal disorders and more particularly in terms of a system comprising a guidewire, a cannulated drill bit, a cannulated inflatable bone tamp and bone void filler and a method for treating a fracture.

In one embodiment, a system includes a guidewire, a working cannula, a cannulated drill bit, a cannulated screwdriver, a cannulated screw, a cannulated IBT and a cannulated bone void filler delivery (BVF) delivery tool. The BVF delivery tool could also be adapted to connect to a cannulated screw to deliver bone void filler through fenestrations in a fenestrated screw. In one embodiment, a method of treating a fracture, for example, a Colles' fracture, using the components of the above-described system is provided. The percutaneous method may manually achieve closed reduction and may be provisionally held with percutaneous pins. In one embodiment, the pins can act as guidewires for subsequent steps. All or most of the subsequent steps can be performed through a working cannula so as to avoid disruption to the surrounding soft tissue. A cannulated drill bit is placed over a guidewire and drilled through bone to create space for subsequent tool placement. In one embodiment, the drill may be advanced toward the opposite cortex, but should not breach the cortex it so that the guidewire remains anchored in the cortex. Once a guidewire is in place, a cannulated inflatable bone tamp (IBT) is placed over the guidewire and inflated to create at least one well-defined bony void. In one embodiment, the IBT can be deflated and re-inflated at a different position so as to create an additional bony void. This can be repeated so as to create multiple voids that span the fracture site.

The positioning of the IBT is determined based on the type and position of the fracture being treated. In one embodiment, the IBT is inflated multiple times to create multiple continuous and/or discontinuous voids. The IBT may have a small maximum inflation volume and a low maximum inflation pressure to assist in a more targeted placement of bony voids. In one embodiment, the IBT may have a mechanism to lock the IBT in place so as to prevent proximal or distal migration of the IBT into previously formed voids. In one embodiment, bone void filler, such as, for example, bone cement, is delivered using a multi-lumen cannula, where one lumen is configured to accommodate a guidewire and a second lumen is configured to accommodate the passage of bone void filler. In one embodiment, a cannulated screw is placed over the guidewire for definitive fixation to bone. The screw may have fenestrations so as to allow for the passage of bone void filler. In one embodiment the screw is placed after the bone void is delivered. The screw may be coated with hydroxyapatite to aid in bony union.

It is envisioned that the system of the present disclosure may be employed to treat fractures of the distal radius, such as, for example, Colles' fracture. It is contemplated that the system of the present disclosure may be employed with other osteal and bone related applications, including those associated with diagnostics and therapeutics. It is further contemplated that the disclosed system may be alternatively employed in a surgical treatment with a patient in a prone or supine position, and/or employs various surgical approaches to the spine, including anterior, posterior, posterior mid-line, lateral, postero-lateral, and/or antero-lateral approaches, and the extremities, such as tibial plateau, calcaneus, proximal humerus as well as other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification, including the appended claims, "treating" or "treatment" of a disease or condition refers to performing a procedure that may include administering one or more materials to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system including a guidewire, a cannulated drill bit, a cannulated inflatable bone tamp (IBT) and bone void filler, cannulated screw and cannulated bone void filler delivery tool as well as related components and methods of employing the surgical system in accordance with the principles of the present disclosure. Alternate embodiments are also disclosed. References will now be made in detail to the exemplary embodiments of the present disclosure, which are illustrated in the accompanying figures. Turning now to FIGS. 1-10, there are illustrated components of a surgical system in accordance with the principles of the present disclosure.

The components of the disclosed system can be fabricated from biologically acceptable materials suitable for medical applications, including metals, synthetic polymers, ceramics and bone material and/or their composites, depending on the particular application and/or preference of a medical practitioner. For example, the components of the disclosed system, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL- ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the disclosed system may have material composites, including the above materials, to achieve various desired characteristics such as strength, rigidity, elasticity, compliance, biomechanical performance, durability and radiolucency or imaging preference. The components of the disclosed system, individually or collectively, may also be fabricated from a heterogeneous material such as a combination of two or more of the above-described materials. The components of the disclosed system may be monolithically formed, integrally connected or include fastening elements and/or instruments, as described herein.

The method and device provided may be used with a fracture of the human forearm. The human forearm consists of two bones, the radius and the ulna. The radius is a long bone that is situated on the thumb side of the forearm, while the ulna is located at the little finger side. The radius lies side by side with the ulna, and it exceeds the ulna both in length and in size. The upper end of the radius is small and articulates with a part of the elbow joint, including the proximal ulna. The bottom end of the radius is large and articulates with two bones of the wrist, or carpus, known as the lunate and scaphoid bones. The inner, or medial side of the distal radius contains an ulnar notch that articulates with the ulna.

The system and methods of the present disclosure are especially suited for treating fractures of long bones, such as, for example, a Colles' fracture or transverse wrist fracture. Such a fracture generally occurs less than one inch from the distal end of the radius. Colles' fractures are commonly noted in younger adults and the elderly where the person tries to break or stop a fall by using his or her hands and arms. Colles' fractures in young adults and children are often associated with sports-related accidents. In the elderly, Colles' fractures are commonly caused by osteoporosis and/or in connection with a fall.

Cancellous bone comprises most of the bone tissue of the extremities of long bones such as the radius. In contrast to cancellous bone, cortical bone tissue is much harder and denser. Cortical bone is layered over cancellous bone, and provides a protective layer and support for long bones such as the radius. At the ends of such bones, however, the cortical bone layer becomes thinner. Where osteoporosis has significantly weakened the cancellous bone, such regions at the ends of long bones become especially prone to fracture and/or collapse.

A form of treating such fractures is by reducing fractured cortical bone and/or compressing cancellous bone within long bones such as the radius. The compression, for example, can be used to form a void or a plurality of voids, which are to receive bone void filler material, such as, for example, bone cement or bone void filler. Bone cement is a flowable material that sets to a hardened condition to provide improved interior support for cortical bone or other therapeutic functions, or both. The compaction of cancellous bone also exerts interior force upon cortical bone, making it possible to elevate or push broken and compressed bone back to or near its original pre-fracture, or other desired, condition. The method and system provided can be used in connection with such bone repair.

In assembly, operation and use, a system, such as, for example, system 10 is used with a surgical procedure for treatment of a fracture, such as, for example, a distal radius fracture, as shown in FIGS. 1-10. For example, system 10, the components of which are shown in FIG. 1, can be used with a surgical procedure for treatment of a fracture in a distal portion of a long bone, for example, a Colles' fracture in the distal radius DR. In some embodiments, system 10 may be employed with other surgical procedures, such as, for example, those described herein.

In use, to treat the Colles' fracture, a medical practitioner obtains access to a surgical site including distal radius DR in any appropriate manner, such as through incision and retraction of tissues. In some embodiments, system 10 may be used in any existing surgical method or technique including open surgery, mini-open surgery, minimally invasive surgery including percutaneous surgical implantation, whereby bone is accessed through a micro-incision, or sleeve that provides a protected passageway to the area. Once access to the surgical site is obtained, the particular surgical procedure is performed for treating the fracture. The components of system 10 are employed to augment the surgical treatment. The components of system 10 can be delivered or implanted as a pre-assembled device or can be assembled in situ. One or all of the components of system 10 may be completely or partially revised, removed or replaced during or after the surgical procedure.

One or a plurality of incisions are made in the body of a patient and a cutting instrument (not shown) creates one or a plurality of surgical pathways and/or access paths for implantation of components of system 10. For example, system 10 (as shown in FIG. 1) is employed with a percutaneous surgical implantation such that a stab incision creates an access path AP for delivering at least one guidewire 12 to the surgical site. A preparation instrument (not shown) can be employed to prepare tissue surfaces of distal radius DR, as well as for aspiration and irrigation of a surgical region according to the requirements of a particular surgical application.

Figure 2:
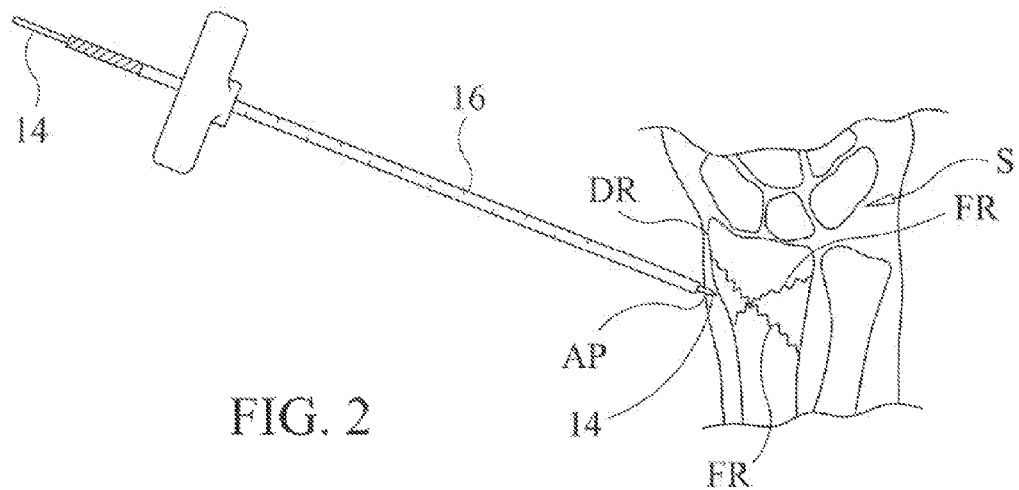
FIG. 2 is a side section view of a component of the system shown in FIG. 1 disposed with bone.
Figure 10:
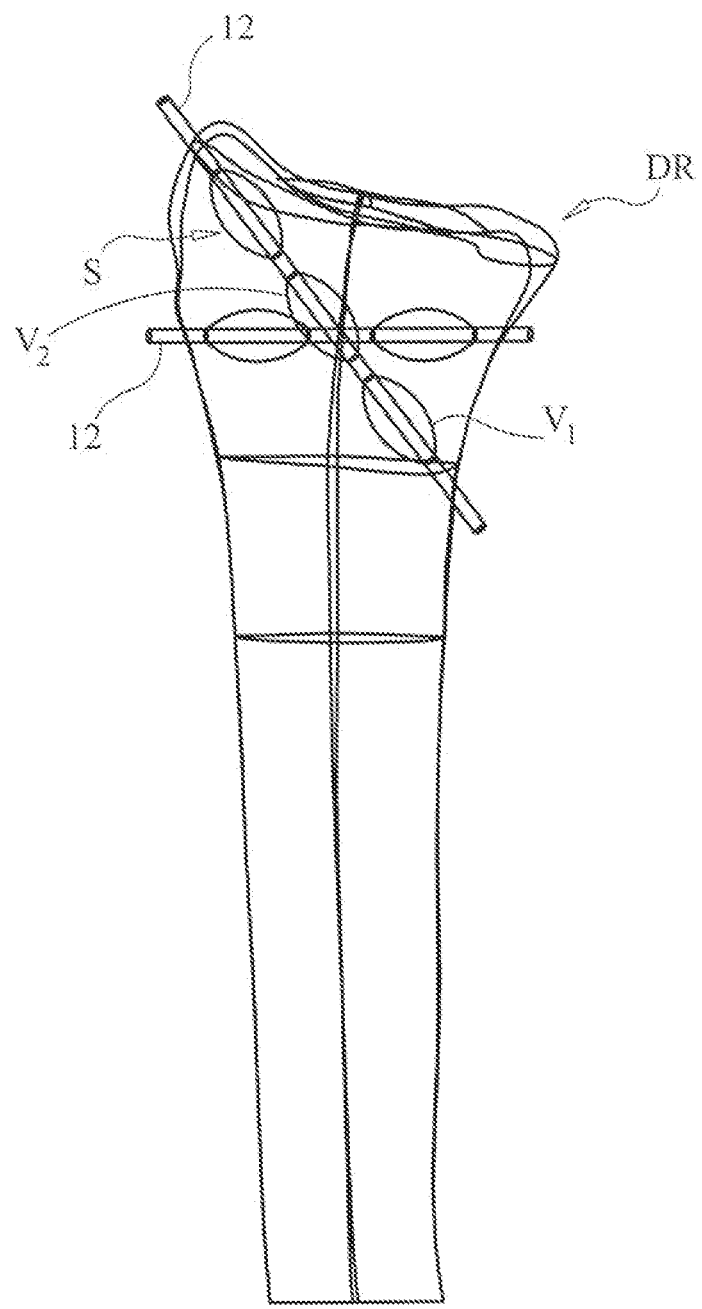
FIG. 10 is a perspective view of components of the system shown in FIG. 1 disposed with bone.

For example, the practitioner may insert a working cannula 16, working cannula 16 having an outer sheath and a stylus 14, into the distal radius DR such that working cannula 16 is in-line with fracture lines FR or transverses fracture lines FR in the distal radius DR, as shown in FIG. 2. In one embodiment, working cannula 16 is positioned in coaxial alignment with one or more fracture lines FR. Upon puncturing the bone, the practitioner removes stylus 14 and inserts guidewire 12 through cannula 16 anchoring a distal end 60 of guidewire 12 to a bone, such as, for example, the radial cortex. Working cannula 16 may be left in place. In one embodiment, working cannula 16 is removed from fracture site S. In one embodiment, the guidewires 12 may be placed without using the working cannula 16. It is contemplated that a plurality of guidewires 12 may be positioned within the distal radius DR transverse to a plurality of fracture lines FR, as shown in FIG. 10. It is also contemplated that multiple guidewires 12 may be placed across fracture lines during the procedure.

Figure 3:
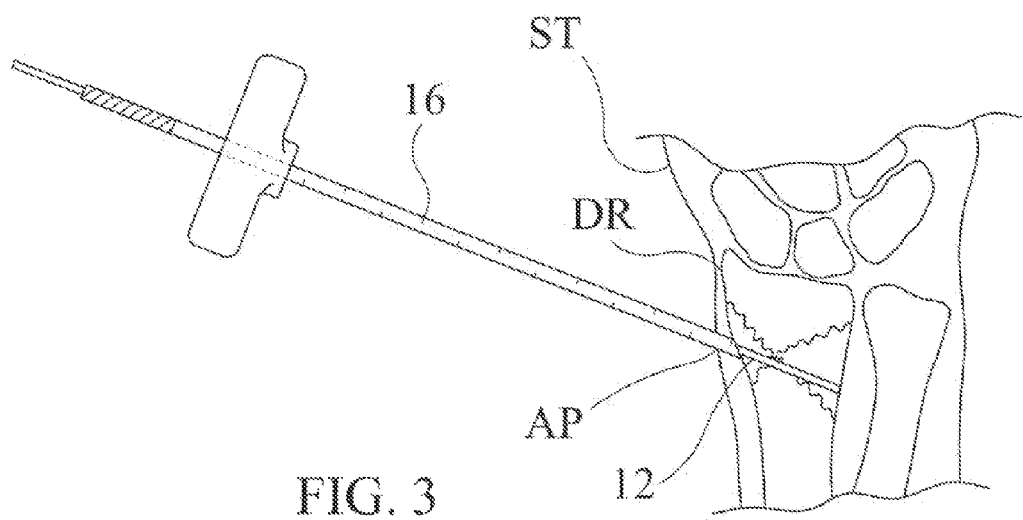
FIG. 3 is a side section view of components of the system shown in FIG. 1 disposed with bone.

As shown in FIG. 3, cannula 16 is positioned through access path AP in tissue, such as, for example, soft tissue ST and is disposed about guidewire 12 to protect against soft tissue damage from the operation of the components of system 10. In one embodiment, cannula 16 has a roughened end configured for frictional engagement with bone such that cannula 16 does not move relative to the bone. In one embodiment, the distal tip of cannula 16 is threaded so as to facilitate anchoring into the bone. In another embodiment, a separate tool is used to hold the cannula 16 in place during the procedure. Still further, in another embodiment, cannula 16 is not used.

Figure 4:
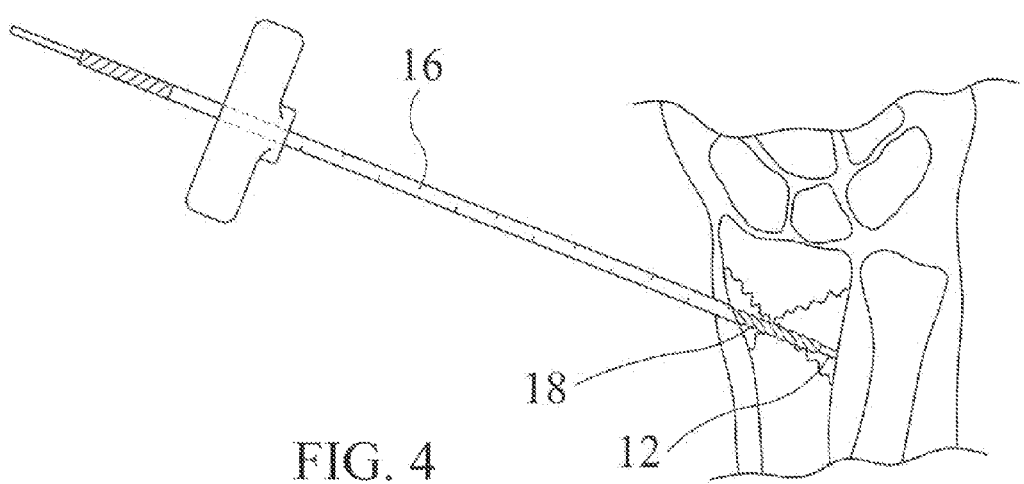
FIG. 4 is a side section view of components of the system shown in FIG. 1 disposed with bone.

A cannulated drill bit 18 is engaged to a tool (not shown) for driving the rotation of drill bit 18. Drill bit 18 is positioned over guidewire 12 and through cannula 16 into fracture site S, as shown in FIG. 4. Drill bit 18 is advanced through the distal radius DR to create a passageway in the distal radius DR configured to receive a cannulated screw 20. Once the passageway is created by drill bit 18, drill bit 18 is removed from the passageway and is withdrawn from cannula 16. The passageway is also used to receive the IBT and/or the bone void filler (BVF) delivery tool.

Figure 5:
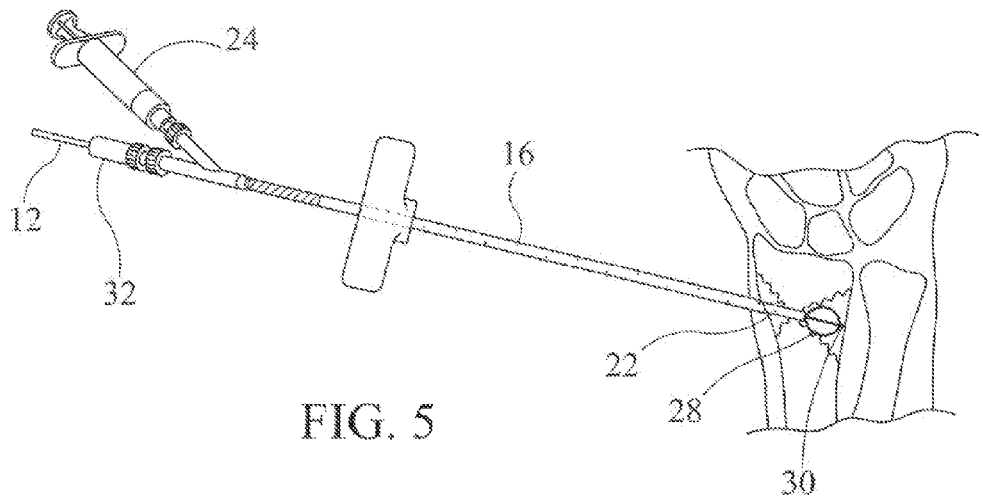
FIG. 5 is a side section view of components of the system shown in FIG. 1 disposed with bone.

A cannulated Inflatable bone tamp (IBT) 22 is then positioned over guidewire 12 and through cannula 16 into the fracture site S, as shown in FIG. 5. IBT 22 includes a syringe 24 configured to store and pump inflatable material through IBT 22. As a plunger of a syringe 24 is compressed into a chamber of syringe 24, inflatable material travels through a first port 26 of IBT 22 and into a balloon 28 causing balloon 28 to expand about a stylet 30 disposed within IBT 22. In the inflated or expanded state, balloon 28 compresses at least a portion of the bone in the fracture site S so as to create at least one void, such as, for example, a first bone void v1, as shown in FIG. 10.

IBT 22 is then deflated to its unexpanded orientation and repositioned to a second position along guidewire 12 spaced from first void v1. Once the first void v1 is created, balloon 28 can be deflated and positioned along guidewire 12 to a second position in the fracture site. In the second position, IBT 22 is anchored to guidewire 12 by a mechanical locking device, such as, for example, a stopper 32 so as to prevent migration of IBT 22 into first void v1 when balloon 28 is being inflated.

After IBT 22 is detachably locked to guidewire 12, IBT 22 is inflated to its expanded orientation to compress a second portion of the distal radius DR in fracture site S so as to create a second bone void v2, as shown in FIG. 10. IBT 22 can be repositioned along guidewire 12 any number of times to create a plurality of voids that are continuous and/or discontinuous and transverse to or along multiple fracture lines. After the desired number of bone voids are created in fracture site S, IBT 22 is removed from fracture site S and cannula 16. In one embodiment, the procedure is used to create a single void using a larger IBT.

Figure 6:
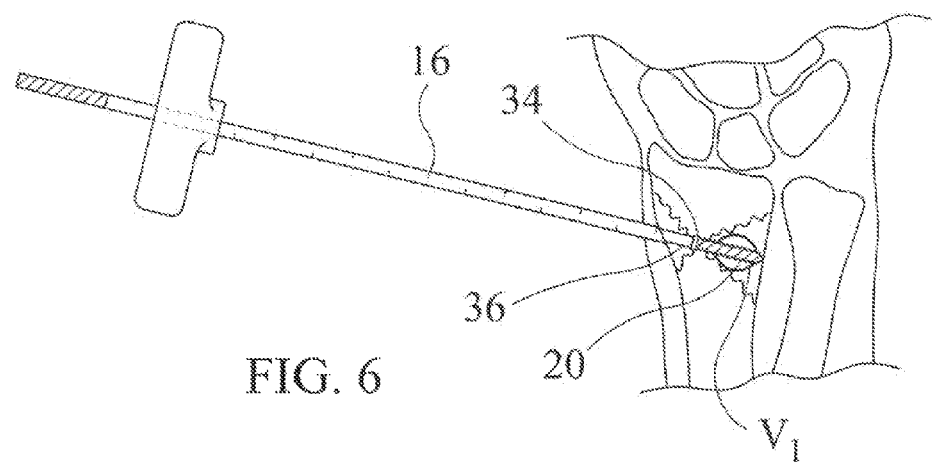
FIG. 6 is a side section view of components of the system shown in FIG. 1 disposed with bone.

In one embodiment, after IBT 22 creates a plurality of bone voids in fracture site S, cannulated screw 20 is positioned within the bone voids. In this embodiment, a head of cannulated screw 20 is engaged to a Philips, hex, tom star or other engaging designed head 34 of a cannulated screwdriver 36, as shown in FIG. 6. Cannulated screw 20 and screwdriver 36 are positioned over guidewire 12 and axially translated through the passageway in the bone created by drill bit 18 via rotation of screwdriver 36 and then anchored into the bone. Screwdriver 36 is then withdrawn from the surgical site and cannula 16. Guidewire 12 is also then removed. In one embodiment, no screws are used. In one embodiment, guidewire 12 is not removed.

Figure 7:
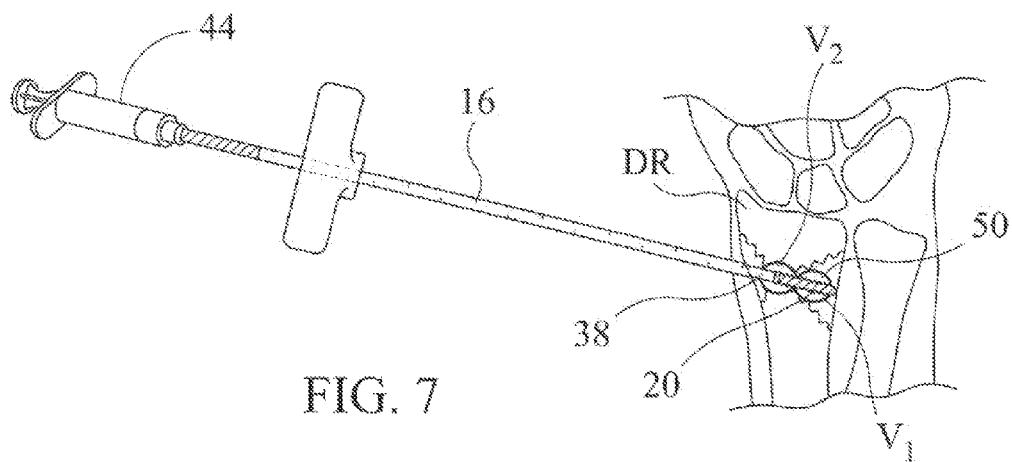
FIG. 7 is a side section view of components of the system shown in FIG. 1 disposed with bone.
Figure 8:
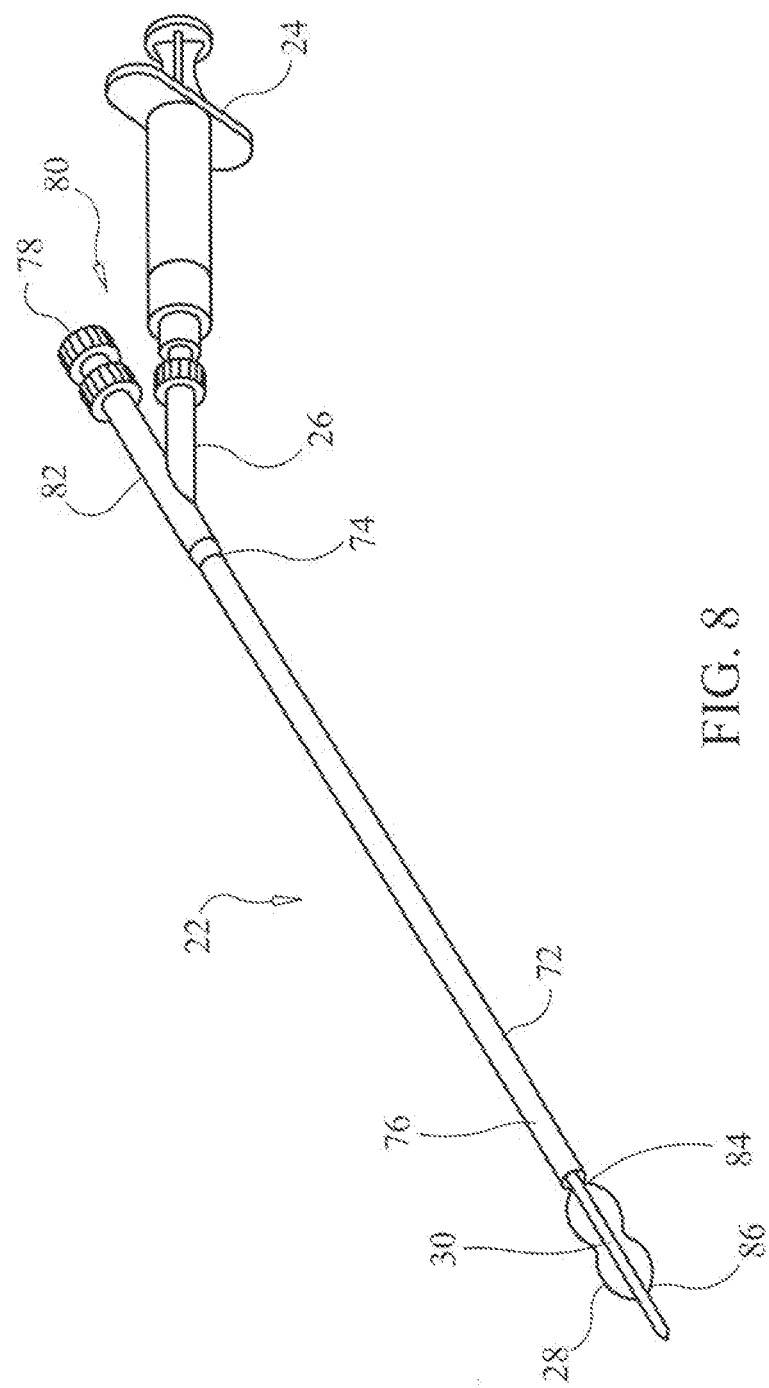
FIG. 8 is a perspective view of a component of the system shown in FIG. 1.
Figure 9:
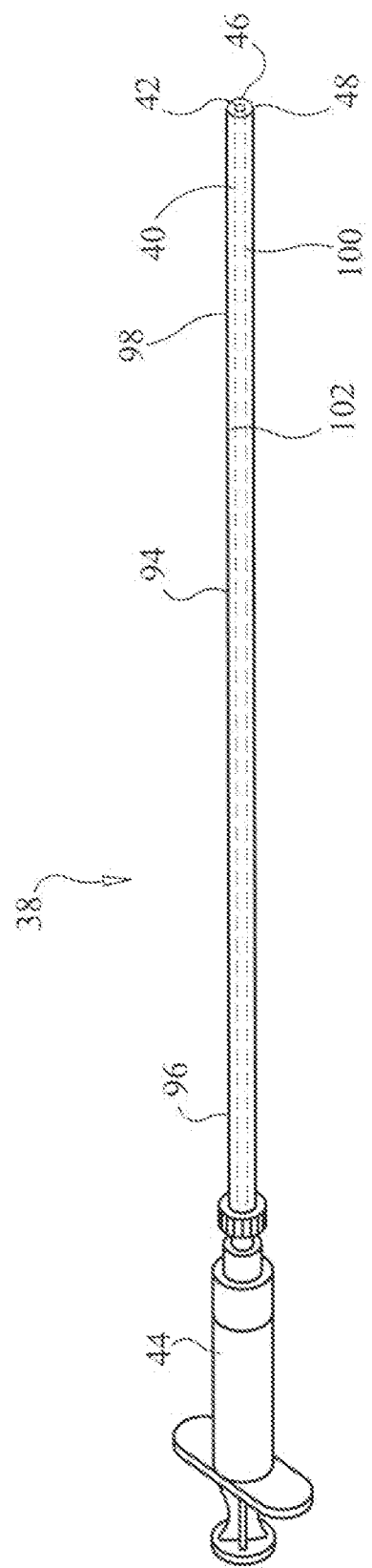
FIG. 9 is a perspective view of a component of the system shown in FIG. 1.

After screw 20 is disposed with bone, a bone void filler (BVF) delivery tool 38 is provided such that guidewire 12 is disposed in a first lumen 40 (FIG. 9) of BVF delivery tool 38 and axially translated such that a first opening 42 (FIG. 9) of BVF delivery tool 38 is disposed within first bone void v1, as shown in FIG. 7. A syringe 44 pumps bone void filler 50 through a second lumen 46 of BVF delivery tool 38 and out of a second opening 48 of BVF delivery tool 38. Bone void filler 50 travels into first bone void v1 filling bone void v1. Bone void filler 50 also travels into passageway 52 of screw 20 via fenestrations 54 filling passageway 52 and enveloping screw 20.

In one embodiment, BVF delivery tool 38 delivers bone void filler 50 into the plurality of bone voids before screw 20 is anchored to the distal radius DR. In this embodiment, guidewire 12 remains in the fracture site S, and BVF delivery tool 38 is positioned over guidewire 12 such that guidewire 12 is disposed in first lumen 40 (FIG. 9) of BVF delivery tool 38 and axially translated such that first opening 42 (FIG. 9) of BVF delivery tool 38 is disposed within first bone void v1, as shown in FIG. 7. Syringe 44 pumps bone void filler 50 through second lumen 46 of BVF delivery tool 38 and out of second opening 48 of BVF delivery tool 38. Bone void filler 50 travels into first bone void v1. Screw 20 is then delivered to bone void v1 causing bone void filler 50 to envelope screw 20.

BVF delivery tool 38 is then repositioned so that BVF delivery tool 38 is disposed within second bone void v2. Syringe 44 is actuated such that bone void filler 50 travels out of second opening 48 of BVF delivery tool 38 into second bone void v2.

A system, such as, for example, surgical system 10 used in carrying out the method for treating fractures described above is provided, as described in further detail below. System 10 includes guidewire 12 or guide pin, such as, for example, a Kirschner wire or Steinman pin for facilitating the use of components of system 10 along the surgical pathway. Guidewire 12 also aligns and/or stabilizes fracture fragments. Guidewire 12 has a cylindrical body. It is contemplated that guidewire 12 is variously configured, such as, for example, oval, oblong, triangular, square, polygonal, irregular, uniform, non-uniform, offset, staggered, undulating, arcuate, variable and/or tapered. Guidewire 12 extends between a proximal end 56 and a distal end 58. Distal end 58 is tapered to a pointed tip 60 configured for anchoring into bone, such as, for example, the cortex of the distal radius DR. In some embodiments, distal end 58 has various surface configurations, such as, for example, rough, threaded, arcuate, undulating, porous, semi-porous, dimpled, polished and/or textured according to the requirements of a particular application. In one embodiment, guidewire 12 has a uniform cross section along its length dimensioned for disposal in a passageway of working cannula 16.

System 10 includes cannulated drill bit 18. Drill bit 18 extends between a proximal end 62 and a distal end 64. Proximal end 62 is configured for engagement with a tool (not shown) used to actuate drill bit 18. Distal end 64 includes helical flutes 66 configured for drilling through bone to create a passageway therethrough. Drill bit 18 includes a cutting edge 68 configured for starting the passageway. Distal end 64 has a diameter of about 1 to 3 mm, preferably about 1.5 to about 2.7 mm. It is contemplated that distal end 64 has a diameter ranging from about 0.5 mm to about 10 mm. Other sizes can be used with the procedure depending on the fracture type, size, location and patient. Drill bit 18 has a passageway 70 defined between ends 62, 64 configured for disposal of guidewire 12. Passageway 70 is dimensioned such that drill bit 18 can axially move along the length of guidewire 12.

System 10 includes a bone reduction device, such as, for example, cannulated inflatable bone tamp (IBT) 22. IBT 22 is configured for positioning over guidewire 12. IBT comprises an outer sleeve 72 extending between a first end 74 and a second end 76. Outer sleeve 72 includes a passageway 78 defined between ends 74, 76 configured for passage of a material used for inflating an inflatable member, such as, for example, balloon 28. End 74 is coupled to a Y-shaped adaptor 80. Adaptor 80 includes first port 26 and a second port 82. First port 26 is coupled to syringe 24 for delivering material to inflate balloon 28. It is contemplated that first port 26 is variously configured to be coupled to various tools capable of delivering the fluid material. Passageway 78 is in fluid communication with first port 26 so that fluid material flowing from first port 26 inflates balloon 28. The fluid material used to inflate balloon 28 can be in the form of a liquid or gas, for example, either saline or compressed air.

Second end 76 of sleeve 72 includes balloon 28 configured to compress cancellous bone debris from a fractured bone and push the debris to a cortical wall region to create a void that can be filled with bone void filler. Balloon 28 extends between a first end 84 and a second end 86. Balloon 28 is made of a material that is expandable under pressure and is capable of withstanding contact with bone fragments, those materials including, for example, silicone, chloroprene, thermoplastic polyurethane (TPU), polyethylene terephthalate (PET), polyamide (Nylon) or any suitable combination thereof.

In one embodiment, IBT 22 is configured to temporarily attach to guidewire 12 while material is provided to inflate IBT 22. Inflatable bone tamp 22 includes stopper 32 configured to detachably lock inflatable bone tamp 22 to guidewire 12 so as to prevent migration of IBT 22 into a void adjacent to the position of IBT 22 when IBT 22 is being inflated. Stopper 32 includes an inner surface defining a passageway configured for frictional engagement with guidewire 12. Stopper 32 is disposed about guidewire 12 and adjacent proximal end 74 of IBT 22 (FIG. 5), preventing migration of IBT 22 in the proximal direction during inflation. It is contemplated that the inner surface of stopper 32 is lined with silicone to create a frictional engagement with guidewire 12 and/or IBT 22. In one embodiment, IBT 22 is threadedly engaged to cannula 16 such that axial translation of IBT 22 is resisted. In one embodiment, sleeve 72 has surface beads to resist the axial translation of IBT 22 within cannula 16.

IBT 22 includes cannulated stylet 30 that extends between a proximal end of second port 82, through sleeve 72, and second end 86 of balloon 28. Balloon 28 is attached to stylet 30 at its first and second ends 84, 86 giving balloon 28 structural integrity such that balloon 28 can be inserted into a surgical site. Stylet 30 includes a passageway defined along its length configured for disposal of guidewire 12.

In one embodiment, system 10 includes cannulated screw 20 configured to fit within a passageway created in bone by cannulated drill bit 18. Screw 20 extends between a first end 88 and a second end 90 configured for engagement with screw driver 36. Screw 20 includes passageway 52 defined between ends 88, 90 and configured for disposal of guidewire 12. In one embodiment, screw 20 includes a plurality of openings or fenestrations 54 along its length that extend from a threaded outer surface 92 into passageway 52. Threaded outer surface 92 is coated with hydroxyapatite to aid in the fusion between screw 20 and a bone.

System 10 includes bone void filler 50 configured for filling voids in the bone generated by IBT 22. It is envisioned that bone void filler 50 may include, for example, materials such as autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables. Bone void filler 50 may have material composites, including the above materials, to achieve various desired characteristics such as strength, rigidity, elasticity, compliance, biomechanical performance, durability and radiolucency or imaging preference.

System 10 includes BVF delivery tool 38. It is contemplated that IBT 22 and BVF delivery tool 38 are combined into one tool capable of performing the functions of IBT 22 and BVF delivery tool 38. BVF delivery tool 38 includes a body 94 extending between a first end 96 and a second end 98. First end 96 is configured for engagement with a syringe 44 that delivers bone void filler 50. It is contemplated that first end 96 is configured for engagement with various tools capable of delivering bone void filler 50. Second end 98 includes first opening 42 and second opening 48. Body 94 includes first lumen 40 defined by a cylindrical tube 100 concentrically disposed within body 94. First lumen 40 is configured for disposal of guidewire 12. Body 94 includes second lumen 46 defined between cylindrical tube 100 and an inner surface 102 of body 100 extending between end 96 and second opening 48. Syringe 44 is in fluid communication with second lumen 46 such that as syringe 44 pumps bone void filler 50 into end 96 of body 94, bone void filler 50 travels through second lumen 46 and out of second opening 48 into a bone void. In one embodiment, the bone filler delivery (BFD) tool is configured to have two lumens, where one of the lumens is configured to go over the guide wire and the other lumen is used for delivery of the BVF material.

System 10 includes a cannulated driving tool, such as, for example, cannulated screwdriver 36 configured for engagement with cannulated screw 20. Screwdriver 36 is cylindrical and has a uniform cross section along its length. It is contemplated that screwdriver 36 is variously shaped, such as, for example, those alternatives described herein. Screwdriver 36 has a diameter of about 2.5 mm. It is contemplated that screwdriver 36 has a diameter from about 1 mm to about 5 mm, depending on the diameter of cannulated screw 20. Screwdriver 36 extends between a first end 104 and a second end 106. First end 104 is configured for engagement with a tool (not shown) that drives the rotation of screwdriver 36. Second end 106 includes an engagement portion, such as, for example, Philips, hex, tom star or other engaging designed head 34. In some embodiments, engagement portion is variously configured to engage various cannulated screws 20, such as, for example, Philips, hex, tom star, slotted head, hex socket head, hexagon external head, frearson head, square socket, square slotted combination head, spanner drilled tamper proof head and combinations thereof. Screwdriver 36 includes a passageway 108 defined between ends 104, 106 configured for disposal of guidewire 12.

System 10 includes cannula 16 having a passageway 110 defined between a proximal end 112 and a distal end 114. Passageway 110 is configured for disposal of guidewire 12, cannulated drill bit 18, cannulated screw 20, BVF delivery tool 38 and/or IBT 22. Cannula 16 includes a smooth outer surface 116 such that cannula 16 prevents damage to surrounding soft tissue during the use of the instruments of system 10 within passageway 110 of cannula 16. Cannula 16 is made of metal and contains markings along outer surface 116 to indicate to a practitioner the depth at which cannula 16 has been placed into a patient's distal radius DR. In one embodiment, distal end 114 includes a roughened surface (not shown) configured for fixing cannula to the surface of the distal radius DR.

As shown in FIG. 1, a kit is provided, including instruments 12, 16, 18, 22, 36 and/or 38. One or all of the instruments of system 10 may be disposable, peel-pack, pre-packed sterile devices. One or all of the components of system 10 may be reusable.

It is contemplated that other agents and materials may be delivered to a surgical site using the disclosed system, in place of or in addition to a bone void filler. These agents include therapeutic polynucleotides or polypeptides. These agents may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite (HA), calcium phosphate and calcium sulfate, biologically active agents, for example, gradual release compositions such as by blending in a bioresorbable polymer that releases the biologically active agent or agents in an appropriate time dependent fashion as the polymer degrades within the patient. Suitable biologically active agents include, for example, Bone Morphogenetic Proteins (BMP), Growth Differentiation Factors (GDF) and cytokines.

In performing a method of treatment using system 10, it can be desirable that balloon 28 not adhere to tissue or other surfaces. Thus, various coatings can be applied to an outside wall of balloon 28, such as, for example, Teflon spray or silicon oil. In one embodiment, a portion of inflatable bone tamp 22 is coated with a radiopaque or fluorescent material that is detectable by medical imaging devices so as to determine orientation and degree of inflation when placed in the bone.

It is envisioned that the use of microsurgical and image guided technologies may be employed to access, view and repair bone deterioration or damage, in conjunction with the expandable devices.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A system for treating a fracture, comprising:
   a bone void filler delivery tool extending along a longitudinal axis between a proximal end and an opposite distal end including an end surface that extends transverse to the longitudinal axis, the tool comprising a first inner surface defining a central first lumen and a second inner surface defining a second lumen that is spaced apart from the first lumen by the first inner surface, the lumens being in communication with openings that extend through the end surface;
   a syringe removably coupled to the proximal end of the tool, the syringe being in fluid communication with the second lumen;
   a guidewire configured for disposal in the first lumen; and
   a drill bit configured for drilling through bone.

2. A system as recited in claim 1, wherein the drill bit is cannulated to define a passageway configured for disposal of the guidewire.

3. A system as recited in claim 1, wherein a distal end of the drill bit comprises a cutting edge configured for starting a passageway in the bone.

4. A system as recited in claim 1, wherein a distal end of the drill bit is fluted.

5. A system as recited in claim 1, wherein a distal end of the drill bit comprises helical flutes.

6. A system as recited in claim 1, wherein a proximal end of the drill bit has a maximum diameter that is greater than that of a distal end of the drill bit.

7. A system as recited in claim 1, wherein a distal end of the drill bit has a diameter of about 0.5 to about 10 mm.

8. A system as recited in claim 1, wherein a distal end of the drill bit has a diameter of about 1 to about 3 mm.

9. A system as recited in claim 1, further comprising a screw removably coupled to the distal end of the tool such that bone void filler disposed in the second lumen travels out of one of the openings and into a passageway in the screw via fenestrations in the screw.

10. A system as recited in claim 9, wherein a threaded outer surface of the screw is coated with hydroxyapatite.

11. A system as recited in claim 1, wherein the proximal end of the tool comprises a fitting having the syringe removably coupled thereto, the syringe being configured such that a bone void filler disposed within the syringe can be delivered into the second lumen from the syringe.

12. A system according to claim 1, further comprising bone cement configured for disposal in the second lumen.

13. A system according to claim 1, further comprising a cannula extending between opposite proximal and distal ends, the cannula comprising an inner surface defining a passageway having the tool disposed therein such that a distal end of the bone void filler delivery tool extends outwardly from the distal end of the cannula.

14. A system according to claim 13, wherein the cannula comprises markings along an outer surface of the cannula configured to indicate to a practitioner a depth at which the cannula is inserted into a patient.

15. A system as recited in claim 13, wherein a distal tip of the cannula is threaded so as to facilitate anchoring into bone.

16. A system for treating a fracture, comprising:
   a cannula extending between opposite proximal and distal ends, the cannula comprising an inner surface defining a passageway;
   a bone void filler delivery tool extending along a longitudinal axis between a proximal end and a distal end including an end surface that extends transverse to the longitudinal axis, the tool being disposed within the passageway such that the distal end of the tool extends outwardly from the distal end of the cannula, the tool comprising a first inner surface defining a central first lumen and a second inner surface defining a second lumen that is coaxial with the first lumen, the second lumen surrounding the first lumen, the lumens each being in communication with opening that extend through the end surface;
   a guidewire disposed in the first lumen;

a syringe removably coupled to a proximal end of the tool, the syringe being in fluid communication with the second lumen;

bone void filler disposed within the syringe; and a screw coupled to the distal end of the bone void filler delivery tool.

17. A system as recited in claim 16, wherein the bone void filler is configured to move from the syringe into the second lumen, and from the second lumen into a passageway in the screw via fenestrations in the screw.

18. A system as recited in claim 16, wherein the first inner surface is permanently fixed relative to the second inner surface.

19. A system as recited in claim 16, wherein the bone void filler comprises bone cement comprising a polymethylmethacrylate-based material.

20. A system as recited in claim 15, wherein:

the cannula comprises markings along an outer surface of the cannula configured to indicate to a practitioner a depth at which the cannula is inserted into a patient; and a distal tip of the cannula is threaded so as to facilitate anchoring into bone.

\* \* \* \* \*